United States Patent
Sakaguchi et al.

(10) Patent No.: US 11,482,331 B2
(45) Date of Patent: Oct. 25, 2022

(54) ASSIST SYSTEM, ASSIST METHOD, AND ASSIST PROGRAM

(71) Applicant: TERUMO KABUSHIKI KAISHA, Tokyo (JP)

(72) Inventors: Yuuki Sakaguchi, Shizuoka (JP); Yoshiyuki Hara, Shizuoka (JP); Yuusuke Sekine, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/887,528

(22) Filed: May 29, 2020

(65) Prior Publication Data

US 2020/0294673 A1 Sep. 17, 2020

Related U.S. Application Data

(63) Continuation of application No. PCT/JP2018/028724, filed on Jul. 31, 2018.

(30) Foreign Application Priority Data

Nov. 30, 2017 (JP) .............................. JP2017-230842

(51) Int. Cl.
*G16H 50/20* (2018.01)
*G16H 40/20* (2018.01)

(52) U.S. Cl.
CPC ............. *G16H 50/20* (2018.01); *G16H 40/20* (2018.01)

(58) Field of Classification Search
CPC ........ G16H 40/20; G16H 70/20; G16H 40/00; G16H 40/67; G16H 40/63; G16H 40/40;
(Continued)

(56) References Cited

U.S. PATENT DOCUMENTS

2011/0166883 A1* 7/2011 Palmer .................. G16H 40/20
  705/3
2012/0004925 A1* 1/2012 Braverman ............ G06Q 10/00
  705/2
(Continued)

FOREIGN PATENT DOCUMENTS

| JP | 2001319041 A | 11/2001 |
| JP | 2013120422 A | 6/2013 |
| JP | 2014157605 A | 8/2014 |

OTHER PUBLICATIONS

Martinez, D. A. (2015). Informing the design and deployment of health information technology to improve care coordination (Order No. 3734764). Available from ProQuest Dissertations and Theses Professional. (1734038048). Retrieved from https://dialog.proquest.com/professional/docview/1734038048 (Year: 2015).*

(Continued)

*Primary Examiner* — Joseph D Burgess
(74) *Attorney, Agent, or Firm* — Buchanan Ingersoll & Rooney PC

(57) ABSTRACT

An assist system that assists an operation of a medical institution, including a learning unit that performs machine learning using medical institution data including operation data relating to the operation of the medical institution and economic data relating to the economic efficiency, patient data relating to a patient in a region to which the medical institution belongs, and environment data relating to environment surrounding the medical institution; and a presentation unit that presents an operation policy for improving the economic efficiency of the medical institution based on a result of the machine learning.

20 Claims, 7 Drawing Sheets

(58) Field of Classification Search
CPC ........ G16H 10/60; G06F 19/00; G06Q 10/06;
G06Q 30/0269; G06Q 10/10; G06Q
10/1095; G06Q 10/063116; G06Q 10/04;
G06Q 10/00; G06Q 10/087; G06Q
10/0637

See application file for complete search history.

(56) References Cited

U.S. PATENT DOCUMENTS

| | | | | |
|---|---|---|---|---|
| 2012/0041770 | A1* | 2/2012 | Philippe | G16H 40/20 705/2 |
| 2014/0012592 | A1* | 1/2014 | Ivanovic | G06Q 10/06395 705/2 |
| 2014/0088989 | A1* | 3/2014 | Krishnapuram | G16H 50/50 705/2 |
| 2014/0229214 | A1 | 8/2014 | Bernier et al. | |
| 2015/0213222 | A1* | 7/2015 | Amarasingham | G16Z 99/00 705/2 |
| 2015/0248532 | A1* | 9/2015 | Rajasenan | G16H 40/20 705/2 |
| 2016/0092641 | A1* | 3/2016 | Delaney | G16H 10/60 705/3 |
| 2016/0342753 | A1* | 11/2016 | Feazell | G16H 10/60 |
| 2016/0378919 | A1* | 12/2016 | McNutt | G16H 20/40 705/3 |
| 2017/0228517 | A1* | 8/2017 | Saliman | G16H 10/20 |
| 2019/0206521 | A1* | 7/2019 | Walpole | G16H 10/20 |
| 2020/0373006 | A1* | 11/2020 | Kubo | G16H 40/20 |

OTHER PUBLICATIONS

D. Abd, J. K. Alwan, M. Ibrahim and M. B. Naeem, "The utilisation of machine learning approaches for medical data classification and personal care system management for sickle cell disease," 2017 Annual Conference on New Trends in Information & Communications Technology Applications (NTICT), 2017 (Year: 2017).*

F. Liu, M. Hirano and P. Liu, "Networking Business Model In Regional Medical Service—Case of Chikamori Medical Group in Kochi, Japan," 2008 IEEE International Conference on Communications, 2008, pp. 5543-5547, doi: 10.1109/ICC.2008.1039. (Year: 2008).*

International Search Report (PCT/ISA/210) dated Oct. 16, 2018, by the Japan Patent Office as the International Searching Authority for International Application No. PCT/JP2018/028724.

Written Opinion (PCT/ISA/237) dated Oct. 16, 2018, by the Japan Patent Office as the International Searching Authority for International Application No. PCT/JP2018/028724.

May 22, 2017 (No. 1892) pp. 40, 41, ISSN 0029-0491, (Nikkei Business), non-official translation (Offense and defense of AI world domination—Part 4 If it does not change it will only become "slave" (14 pages).

Hitachi Social Innovation Forum 2016, Oct. 27, 2016 (receive date), (Hitachi, Ltd.), non-official translation (Medical innovation by utilization of healthcare information—Optimizing care cycle with analytics integrated medical knowledge and healthcare data) (1 page).

An English Translation of the International Search Report (Form PCT/ISA/210) and the Written Opinion of the International Searching Authority (Form PCT/ISA/237) dated Oct. 16, 2018, by the Japanese Patent Office in corresponding International Application No. PCT/JP2018/028724. (7 pages).

Office Action (Notice of Reasons for Refusal) dated Jul. 19, 2022, by the Japanese Patent Office in corresponding Japanese Patent Application No. 2019-557005 and an English Translation of the Office Action. (7 pages).

* cited by examiner

| MEDICAL INSTITUTION NAME | ADDRESS | MEDICAL TREATMENT SUBJECT | BED | AMBU-LANCE | MACHINE a | ... | LAYOUT | CLINICAL PATH | POLICY |
|---|---|---|---|---|---|---|---|---|---|
| A | × × × | SURGERY, INTERNAL MEDICINE | 25 | 1 | 2 | ... | SKETCH | SCHEDULE TABLE | × × × |
| B | × × × | OPHTHALMOLOGY | 0 | 0 | 0 | ... | SKETCH | SCHEDULE TABLE | × × × |
| C | × × × | OTOLARYNGOLOGY | 0 | 0 | 5 | ... | SKETCH | SCHEDULE TABLE | × × |
| D | × × × | INTERNAL MEDICINE | 50 | 1 | 10 | ... | SKETCH | SCHEDULE TABLE | × × |

| MEDICAL INSTITUTION NAME | DOCTOR NAME | MEDICAL TREATMENT SUBJECT | CLINICAL EXPERIENCE | SURGERY EXPERIENCE | WORK SCHEDULE |
|---|---|---|---|---|---|
| A | O | SURGERY | 20 YEARS | SURGERY HISTORY TABLE | SCHEDULE TABLE |
| | P | SURGERY | 5 YEARS | SURGERY HISTORY TABLE | SCHEDULE TABLE |
| | Q | INTERNAL MEDICINE | 6 YEARS | SURGERY HISTORY TABLE | SCHEDULE TABLE |
| | R | INTERNAL | 25 YEARS | SURGERY HISTORY TABLE | SCHEDULE TABLE |

| IDENTIFICATION ID | PATIENT NAME | ADDRESS | AGE | LIVING HISTORY | HEALTH CONDITION | GENETIC INFORMATION |
|---|---|---|---|---|---|---|
| × × × | S | × × × | 25 | ELECTRONIC MEDICAL RECORD | MEDICAL EXAMINATION RESULTS, INTERVIEW RESULTS | DNA TEST RESULTS |
| × × × | T | × × × | 45 | ELECTRONIC MEDICAL RECORD | MEDICAL EXAMINATION RESULTS, INTERVIEW RESULTS | DNA TEST RESULTS |
| × × × | U | × × × | 33 | ELECTRONIC MEDICAL RECORD | MEDICAL EXAMINATION RESULTS, INTERVIEW RESULTS | DNA TEST RESULTS |
| × × × | V | × × × | 8 | ELECTRONIC MEDICAL | MEDICAL EXAMINATION RESULTS, INTERVIEW | DNA TEST RESULTS |

| | JUNE 1 | JUNE 2 | JUNE 3 |
|---|---|---|---|
| WEATHER | RAIN | RAIN | RAIN |
| TEMPERATURE | 20°C | 17°C | 18°C |
| HUMIDITY | 80% | 75% | 70% |
| SUNSHINE HOURS | 4 HOURS | 3 HOURS | 5 HOURS |

| MEDICAL INSTITUTION NAME | OUTPATIENT WAITING | NUMBER OF HOSPITALIZED PATIENTS | AVAILABLE BEDS |
|---|---|---|---|
| A | 10 SURGERIES, 20 INTERNAL MEDICINE | 20 | 5 |
| B | 5 OPHTHALMOLOGY | 0 | 0 |
| C | 13 OTOLARYNGOLOGY | 0 | 0 |
| D | 0 INTERNAL MEDICINE, 23 OBSTETRICS, 21 PEDIATRICS | 35 | 15 |

| MEDICAL INSTITUTION NAME | SURGERY SUCCESS RATE | PATIENT SATISFACTION |
|---|---|---|
| A | 88% | HIGH |
| B | 77% | NORMAL |
| C | 65% | HIGH |
| D | 70% | LOW |

| MEDICAL INSTITUTION NAME | BALANCE OF PAYMENTS | PROFIT RATE |
|---|---|---|
| A | ¥2000,000 | 5.1% |
| B | ¥2500,000 | 8.3% |
| C | ¥1200,000 | 4.2% |
| D | ¥3000,000 | 11.3% |

- MANAGEMENT POLICIES TO IMPROVE ECONOMIC EFFICIENCY:

INPATIENTS ARE SWITCHED TO OUTPATIENTS WHEN THEY BECOME CHRONIC

IT IS GOOD TO MAKE DISTANCE BETWEEN NURSE STATION AND BED CLOSER

IT IS ADVISABLE THAT HIGHLY QUALIFIED DOCTOR SHOULD BE IN CHARGE OF HIGHLY DIFFICULT SURGERY

- BASIS FOR PRESENTATION:

THE NUMBER OF PATIENTS IS EXPECTED TO INCREASE IN THE FUTURE.
  SWITCHING TO THE ABOVE OPERATION POLICY WILL INCREASE TURNOVER RATIO AND IMPROVE ECONOMIC EFFICIENCY.

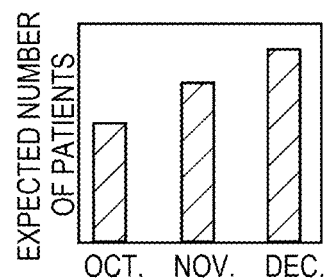

EXPECTED DISEASE NAME: ISCHEMIC HEART DISEASE

NECESSITY OF MEDICAL TREATMENT CONSULTATION: HIGH

RECOMMENDED MEDICAL INSTITUTIONS: MEDICAL INSTITUTION A

PROPOSAL OF MEDICAL TREATMENT SCHEDULE:

| JULY 1 | JULY 2 | JULY 3 | JULY 4 | JULY 5 | JULY 6 |
|---|---|---|---|---|---|
| CONSULTATION | HOSPITALIZATION | INSPECTION | SURGERY | INSPECTION | DISCHARGE |

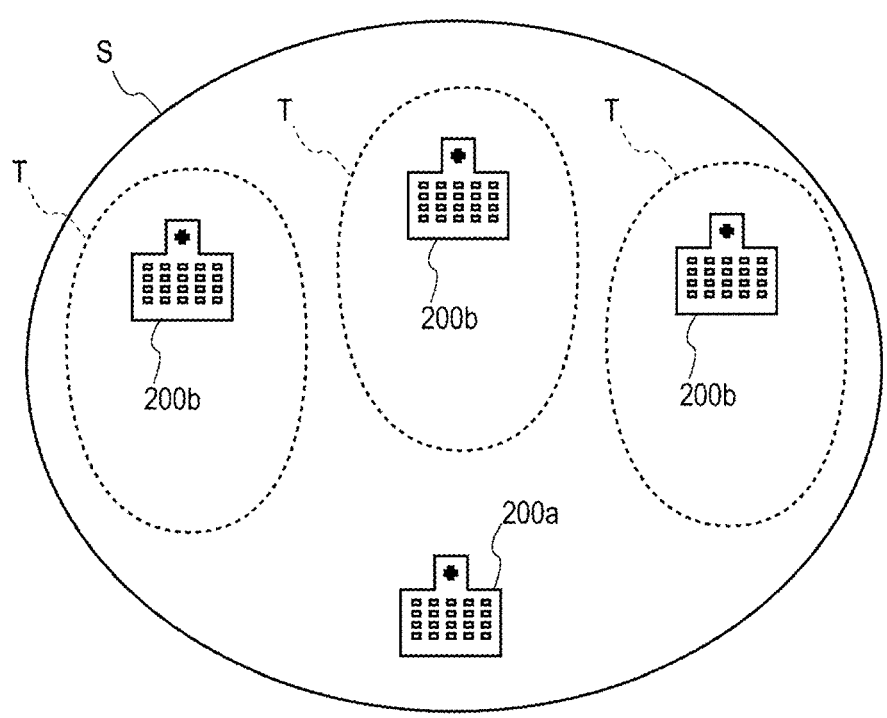

ASSIST SYSTEM, ASSIST METHOD, AND ASSIST PROGRAM

CROSS-REFERENCES TO RELATED APPLICATIONS

This application is a continuation of International Application No. PCT/JP2018/028724 filed on Jul. 31, 2018, which claims priority to Japanese Application No. 2017-230842 filed on Nov. 30, 2017, the entire content of both of which is incorporated herein by reference.

FIELD OF THE DISCLOSURE

The present disclosure generally relates to an assist system, an assist method, and an assist program for assisting the operation of the medical institution.

BACKGROUND DISCUSSION

In recent years, the development of a system for automatically performing medical-related tasks has been promoted. For example, Japanese Patent Application Publication No. 2013-120422 discloses a system that automatically creates a clinical path using patient disease information and clinical path candidates. According to such a system, the management of the medical institution can be made more efficient.

However, the clinical path created by the system disclosed in Japanese Patent Application Publication No. 2013-120422 does not consider the economics of medical institutions. Therefore, the created clinical path may, for example, provide patients with excessively high-quality medical care, and also reduce the economic efficiency of medical institutions. As described above, it is preferable that the operation of the medical institution is performed in consideration of the economic efficiency of the medical institution.

However, the operation of the medical institution is affected by patients in a region to which the medical institution belongs, the surrounding environment, and the like. In addition, the patients in the region to which the medical institution belongs and the surrounding environment change every moment. For this reason, it is difficult for, for example, a manager of the medical institution to perform optimal management that improves the economic efficiency in consideration of the environment surrounding the medical institution. Furthermore, since the medical institutions are concentrated in some regions, and management decisions can be necessary to survive, there is a demand from medical institution managers and the like to improve the operation of the medical institution more efficiently in order to improve the economic efficiency.

SUMMARY

An assist system, an assist method, and an assist program are disclosed that can efficiently improve the operation of a medical institution so that the economic efficiency of the medical institution can be improved.

According to an aspect of the present disclosure, an assist system is disclosed that assists an operation of a medical institution, including a learning unit that performs machine learning using medical institution data including operation data relating to the operation of the medical institution and economic data relating to an economic efficiency, patient data relating to a patient in a region to which the medical institution belongs, and environment data relating to environment surrounding the medical institution; and a presentation unit that presents an operation policy for improving the economic efficiency of the medical institution based on a result of the machine learning.

According to another aspect of the present disclosure, an assist method of assisting an operation of a medical institution is disclosed, the method including performing machine learning using medical institution data including operation data relating to the operation of the medical institution and economic data relating to the economic efficiency, patient data relating to a patient in a region to which the medical institution belongs, and environment data relating to environment surrounding the medical institution; and presenting an operation policy for improving the economic efficiency of the medical institution based on a result of the machine learning.

A non-transitory computer readable medium (CRM) storing computer program code executed by a computer processor that executes a process of assisting an operation of a medical institution is disclosed, the process comprising: performing machine learning using medical institution data including operation data relating to the operation of the medical institution and economic data relating to an economic efficiency, patient data relating to a patient in a region to which the medical institution belongs, and environment data relating to environment surrounding the medical institution; and presenting an operation policy for improving the economic efficiency of the medical institution based on a result of the machine learning.

The present disclosure presents an operation policy that can improve the economic efficiency of a medical institution based on the results of machine learning using medical institution data, patient data, and environment data. Therefore, when a medical institution manager or the like operates the medical institution based on the presented operation policy, it can improve the operation of medical institutions efficiently and improve the economic efficiency.

BRIEF DESCRIPTION OF THE DRAWINGS

FIG. 4A is a diagram illustrating a structure of medical institution data of the assist system according to an embodiment disclosed here.

FIG. 4B is a diagram illustrating a structure of medical institution data of the assist system according to an embodiment disclosed here.

FIG. 4C is a diagram illustrating a structure of patient data of the assist system according to an embodiment disclosed here.

FIG. 4D is a diagram illustrating a structure of environment data of the assist system according to an embodiment disclosed here.

FIG. 4E is a diagram illustrating a structure of environment data of the assist system according to an embodiment disclosed here.

FIG. 4F is a diagram illustrating a structure of quality data of the assist system according to an embodiment disclosed here.

FIG. 4G is a diagram illustrating a structure of economic data of the assist system according to an embodiment disclosed here.

FIG. 6A is a diagram illustrating a content displayed on a display of a medical institution terminal in a presentation step of FIG. 5.

FIG. 6B is a diagram illustrating a content displayed on a display of a patient terminal in a presentation step of FIG. 5.

FIG. 7 is a schematic diagram illustrating a geographical range that is capable of being assisted by each medical institution belonging to a region.

DETAILED DESCRIPTION

Figure 1:
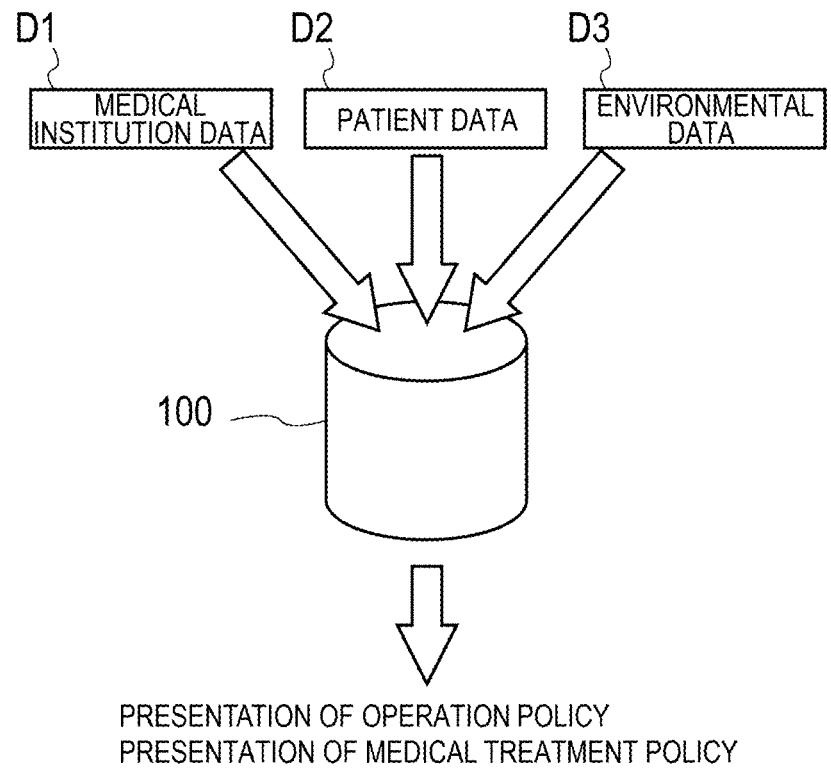
FIG. 1 is a diagram illustrating an outline of an assist system according to an embodiment disclosed here.

Set forth below with reference to the accompanying drawings is a detailed description of embodiments of an assist system, an assist method, and an assist program for assisting the operation of the medical institution representing examples of the inventive assist system, the assist method, and the assist program for assisting the operation of the medical institution disclosed here. In the description of the drawings, the same elements will be denoted by the same reference symbols, without redundant description. In addition, dimensional ratios in the drawings are exaggerated for convenience of explanation, and may differ from the actual ratios.

Figure 2:
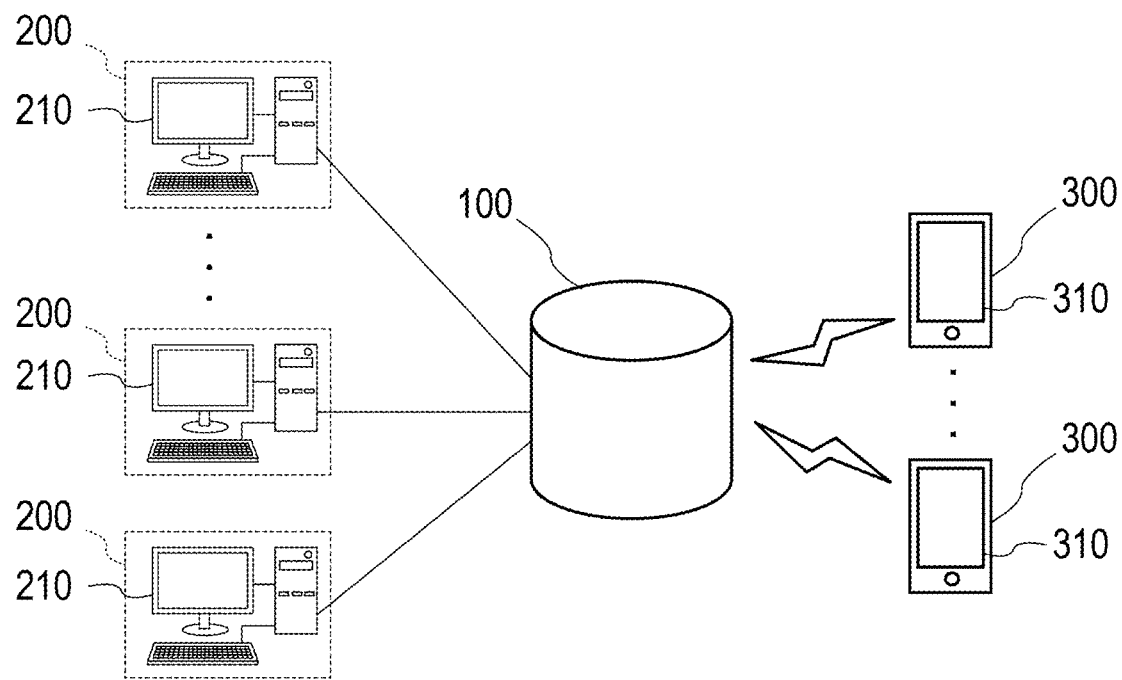
FIG. 2 is a diagram illustrating a state where the assist system according to an embodiment is connected to a medical institution terminal and a patient terminal via a network.
Figure 3A:
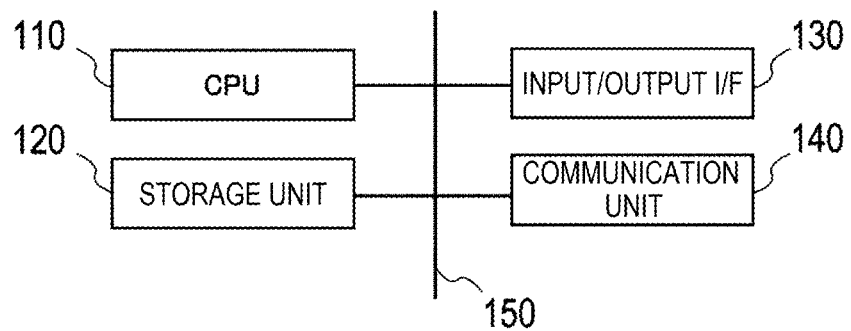
FIG. 3A is a block diagram illustrating a hardware configuration of an assist system according to an embodiment disclosed here.
Figure 3B:
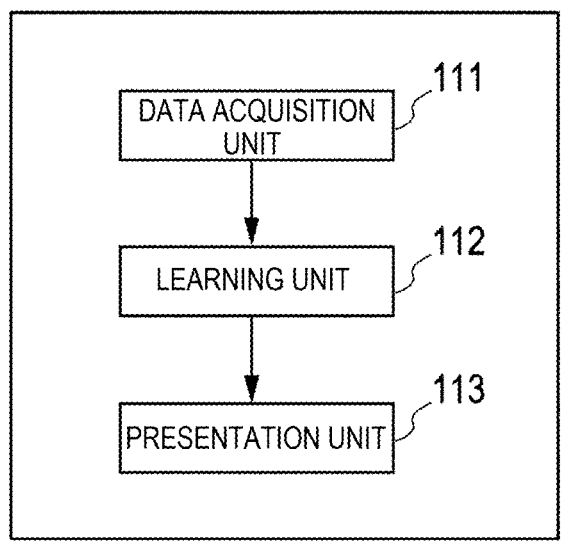
FIG. 3B is a block diagram illustrating a functional configuration of the assist system according to an embodiment disclosed here.

FIGS. 1 and 2 are diagrams for explaining the entire configuration of an assist system 100 according to the embodiment disclosed here. FIGS. 3A and 3B are diagrams for explaining each part of the assist system 100. FIGS. 4A to 4G are diagrams for explaining data handled by the assist system 100.

As illustrated in FIG. 1, the assist system 100 performs machine learning using medical institution data D1, patient data D2, environment data D3, and other data, and the like, presents an operation policy to improve the economic efficiency of each of a plurality of medical institutions belonging to a region, and also presents a medical treatment policy to residents (patients) in the region. In the present specification, "medical institution" refers to a facility where a doctor provides medical care to a patient, and can include a hospital, a clinic, and the like. The "region" is not particularly limited, but can be, for example, a region divided by municipalities, prefectures, or countries.

As illustrated in FIG. 2, the assist system 100 is connected to a medical institution terminal 200 of each medical institution and a patient terminal 300 of each patient via a network, and can be configured as a server that transmits and receives data between the medical institution terminal 200 and the patient terminal 300. The network may employ, for example, a wireless communication system using a communication function such as WiFi® or Bluetooth®, other non-contact wireless communication, or wired communication. Hereinafter, the assist system 100 will be described in detail.

First, the hardware configuration of the assist system 100 will be described.

The assist system 100 is not particularly limited, but can be configured of, for example, a mainframe or a computer cluster. The assist system 100 includes a central processing unit (CPU) 110, a storage unit 120, an input and output interface (output I/F) 130, and a communication unit 140, as illustrated in FIG. 3A. The CPU 110, the storage unit 120, the input and output UF 130, and the communication unit 140 are connected to a bus 150, and exchange data and the like with each other via the bus 150. Hereinafter, each unit will be described.

The CPU 110 is configured to control each unit and executes various arithmetic processes according to various programs stored in the storage unit 120.

The storage unit 120 can be configured to include a read only memory (ROM) that stores various programs and various data, a random access memory (RAM) that temporarily stores programs and data as a work region, and disk that stores various programs and various data including an operating system.

In accordance with an embodiment, the input and output I/F 130 is an interface for connecting input devices such as a keyboard, a mouse, a scanner, and a microphone and output devices such as a display, a speaker, and a printer.

The communication unit 140 can be an interface for communicating with the medical institution terminal 200, the patient terminal 300, and the like.

Next, main functions of the assist system 100 will be described.

The storage unit 120 stores various data such as medical institution data D1, patient data D2, environment data D3, and other data. In addition, the storage unit 120 stores an assist program.

The CPU 110 functions as a data acquisition unit 111, a learning unit 112, and a presentation unit 113 by executing the assist program stored in the storage unit 120, as illustrated in FIG. 3B. Hereinafter, each unit will be described.

First, the data acquisition unit 111 will be described.

The data acquisition unit 111 is configured to acquire the medical institution data D1, the patient data D2, the environment data D3, and other data for machine learning. Immediately after the introduction of new treatment methods, new devices, new drugs, and the like, the population (i.e., training data) is relatively small, and thus there is a possibility that sufficient accuracy may not be obtained by machine learning, or that the result of machine learning may be greatly influenced by one sample. Therefore, it is preferable that the medical institution data D1, the patient data D2, the environment data D3, and other data for machine learning are obtained from a plurality of the medical institutions over a predetermined period.

The medical institution data D1 can include operation data D11 relating to the operation of a plurality of medical institutions and operation result data D12 relating to the results of the operation of each of the medical institutions.

As the operation data D11, as illustrated in FIGS. 4A and 4B, for example, data such as names (medical institution names), addresses, medical treatment subjects, a number of owned equipment (equipment including beds, ambulances, medical equipment, and office equipment), layouts, clinical paths, policies, doctors, and the like of each medical institution are given. Further, the operation data D11 may include information (for example, whether or not primary percutaneous coronary intervention (PCI) for acute myocardial infarction can be performed) on whether or not each surgery can be performed. Further, as illustrated in FIG. 7, the operation data D11 may include, for each disease, information on a geographical range T (for example, in a case of a disease that should be treated within one hour, such as acute myocardial infarction, a geographical range in which the patient can be transported by ambulance within one hour) that can be handled by each of medical institutions 200a and 200b in a case where a patient is urgently transported. In accordance with an embodiment, the operation data D11 can be stored in the storage unit 120 in a state of being linked to geographical information of each medical institution.

The layout data can be configured by a sketch of the medical institution indicating positions and distances of each facility, an examination room, an examination room, an operating room, a nurse station, a general ward, an intensive care unit (ICU), a high care unit (HCU), and the like. The clinical path data can be configured by, for example, a schedule table that summarizes a schedule from hospitalization to discharge (including surgery and examination) of a plurality of patients. The policy data can include, for example, data on education policies such as training, data on medical policies such as priority medical care, and the like. Further, as illustrated in FIG. 4B, the doctor data D11a can include, for example, data such as a doctor name, a medical treatment subject, a medical treatment experience, a surgery experience, and a work schedule. The doctor data D11a can be stored in the storage unit 120 in a state of being linked to each doctor. Note that, in a case where the doctor moves to another region, the assist system 100 may move the doctor data D11a of the moved doctor to another assist system that assists the operation of the medical institution in another region. A data movement method is not particularly limited. For example, in a case where the assist system 100 is connected to another assist system via a network, the moved doctor data D11a can be moved to another assist system via the communication unit 140 and the network.

The operation result data D12 can include, for example, congestion data D12a, quality data D12b, and economic data D12c. The congestion data D12a is not particularly limited as long as it is data relating to a congestion status of each medical institution, and includes, for example, data such as the number of outpatients waiting, the number of hospitalized patients, and the number of empty beds, as illustrated in FIG. 4E. The quality data D12b is not particularly limited as long as it is data on the quality of medical care provided by each medical institution, and as illustrated in FIG. 4F, for example, data such as a success rate of surgery by medical care provided by each medical institution, patient satisfaction, and information on prognosis are included. The economic data D12c is not particularly limited as long as it is data on the economic efficiency of each medical institution, and as illustrated in FIG. 4G, for example, the balance and profit rate of each medical institution are listed. The congestion data D12a, the quality data D12b, and the economic data D12c are stored in the storage unit 120 in a state of being linked to each medical institution.

The assist system 100 extracts management problems in that by using the operation data D11 and the operation result data D12 for machine learning of the learning unit 112 described later, for example, the economic efficiency of the medical institution can deteriorate due to a large number of equipment in stock, the economic efficiency can deteriorate due to the inefficiency in the layout and clinical path of the medical institution, the economic efficiency can deteriorate since insufficient physician training can lead to poor patient satisfaction, and the economic efficiency can deteriorate since other medical institutions belonging to the same region are receiving priority medical care, and patients are deprived of other medical institutions, and the operation policy can be presented to each medical institution.

The data acquisition unit 111 is configured to acquire patient data D2 from the medical institution terminal 200 of each medical institution.

The patient data D2 is not particularly limited as long as it is data on the patient, as illustrated in FIG. 4C, for example, data such as a patient identification ID (for example, my number), a patient name, an address, an age, a medical history, a health status, genetic information, and the like are included. The patient data D2 can be stored in the storage unit 120 in a state of being linked to each patient. The history data can be configured of, for example, an electronic medical record. The health condition data can be configured of, for example, a medical examination result and an interview result. The genetic information may include not only the genetic information of the patient himself or herself, but also the genetic information of a relative. The genetic information can be configured of, for example, DNA test results. Note that the genetic information can be used, for example, to determine whether or not a disease is strongly affected by genetic factors when determining a disease of a person to be examined.

In accordance with an aspect, the assist system 100 uses the patient data D2 for machine learning of the learning unit 112 described later to present an operation policy for improving the economic efficiency of each medical institution and a medical treatment policy for each patient in consideration of the influence of the patient data D2 on the operation and the like of the medical institution (for example, the number of patients is expected to increase in the future due to the presence of potential patients of pre-diabetes and pre-myocardial infarctions, and the economic efficiency can be improved by operating according to the increase in the number of patients).

The data acquisition unit 111 is configured to acquire patient data D2 from the medical institution terminal 200 of each medical institution and the patient terminal 300 of each patient.

The environment data D3 is not particularly limited as long as it is data on the environment surrounding each medical institution, and as illustrated in FIG. 4D, for example, data on the weather, temperature, humidity, sunshine duration, and diseases that are prevalent in the region, of the surrounding environment, can be exemplified.

The assist system 100 uses the environment data D3 for machine learning of the learning unit 112 described later to present an operation policy for improving the economic efficiency of each medical institution and a medical treatment policy for each patient in consideration of the influence of the surrounding environment on the operation and the like of the medical institution (for example, the number of patients is expected to increase due to the spread of colds and flu in the future, and the economic efficiency can be improved by operating according to the increase in the number of patients).

The data acquisition unit 111 can acquire the environment data D3 from the Internet, for example.

Other data include medical data on medical knowledge, traffic data on transportation means for accessing each medical institution, reuse data, and the like. Examples of the medical data include disease data relating to the disease (disease name, symptoms, necessity of medical treatment, and the like), treatment data relating to treatments (treatment method, time required for treatment, necessary equipment and drugs, wholesale price of the necessary equipment and drugs, and the like), and data relating to a medical insurance system and the like. Examples of the traffic information include information such as fares and required time by transportation means such as taxis, buses, and trains. Examples of the reuse data include information on whether the medical device can be reused by performing cleaning or sterilization. The medical device can be, for example, a single-use medical device, but may be a medical device (a component part of a medical device) other than the single-use medical device. Further, the reuse data can include, for example, information on surplus medicines. Examples of the surplus medicines include information on whether or not a medicine (for example, a liquid medicine) stored in a predetermined amount in a container such as a bottle can be used for a plurality of patients. For example, in a case where a drug stored in a specific container can be administered to patient A and a drug stored in a similar container can be administered to patient B, the drug is treated as reusable.

The data acquisition unit 111 can acquire other data from, for example, the Internet or from electronic data of medical specialty books captured by a scanner or the like. Note that, the reuse data can be acquired in real time from, for example, a hospital information system of a medical institution that owns a medical device or a medicine to be reused.

Next, the learning unit 112 will be described.

The learning unit 112 performs the machine learning by using the medical institution data D1, the patient data D2, the environment data D3, and other data for machine learning, acquired by the data acquisition unit 111. Note that, in this specification, "machine learning" refers to analyzing input data using an algorithm, extracting useful rules and criteria from the analysis result, and developing the algorithm. The algorithm of machine learning can be generally classified into supervised learning, unsupervised learning, reinforcement learning, and the like. In the algorithm of the supervised learning, a data set of an input and a result is provided to the learning unit 112 to perform the machine learning. In the algorithm of the unsupervised learning, a large amount of input data alone is provided to the learning unit 112 to perform the machine learning. The algorithm of the reinforcement learning changes the environment based on the solution output by the algorithm, and makes corrections based on the reward of how correct the output solution is.

The algorithm used by the learning unit 112 for machine learning may be any of supervised learning, unsupervised learning, and reinforcement learning, and the learning unit 112 uses one or a plurality of algorithms to extract rules, criteria, and the like related to the economic efficiency of the medical institution.

Specifically, for example, the learning unit 112 may use a regression or classification algorithm of the supervised learning, and the like to perform the machine learning of the relationship between the operation data D11, the congestion data D12a, the quality data D12b, the patient data D2, the environment data D3, and other data with the economic data D12c, and extract the rules and criteria for the economic efficiency of the medical institution. With this, the presentation unit 113, which will be described later, can present an operation policy that improves the economic efficiency of the medical institution in consideration of, for example, the patients in the region to which the medical institution belongs and the environment around the medical institution.

In addition, the learning unit 112 may apply the algorithm of the unsupervised learning clustering to the medical institution data D1, the patient data D2, the environment data D3, and other data to extract rules and criteria for the economic efficiency of the medical institution. With this, for example, the learning unit 112 can extract common points of the operation of the medical institution with the excellent economic efficiency, and extract the medical fields that are insufficient in the region by clustering the local population (including current and potential patients), and comparing the clustering results with the fields of priority medical care of local medical institutions. In addition, as illustrated in FIG. 7, for example, the learning unit 112 may cluster information on whether or not each surgery of each of the medical institutions 200a and 200b in each region S can be performed, and information on the geographical range T that each of the medical institutions 200a and 200b can handle for each disease in a case where a patient is urgently transported so as to extract which surgery is insufficient in which geographical range of the region S.

In addition, the learning unit 112 uses a supervised learning regression or classification algorithm to present a medical treatment policy to each patient so as to perform the machine learning on the relationship between the patient data D2, the environment data D3, and medical data (including disease data). With this, the presentation unit 113 described later can expect the patient's disease from the latest patient data D2 and environment data D3. In addition, as described above, the learning unit 112 uses a regression or classification algorithm of the supervised learning, and the like to perform the machine learning of the relationship between the operation data D11, the congestion data D12a, the quality data D12b, the patient data D2, the environment data D3, and other data (including traffic data) with the economic data D12c, and extract the rules and criteria for the economic efficiency of the medical institution. Thus, for example, the presentation unit 113, which will be described later, can present treatment schedules (including clinical paths) in consideration of the patient's address and transportation means, the priority medical care of the medical institution, recommended medical institutions, the congestion status of the medical institution, and the economic efficiency of the medical institution.

In addition, the learning unit 112 can perform the machine learning on information that contributes to the determination of reuse of medical devices based on information for example, whether or not the medical devices used for surgery and medical treatment are reusable, if the medical devices are reusable, what kind of method (washing and sterilization method) is employed to reuse the medical devices, and which component of the medical device can be reused. In addition, the learning unit 112 can perform the machine learning on information that contributes to the determination of reuse of medicines based on information for example, whether or not the medicines used for surgery and medical treatment are reusable, and if the medicines are reusable, what kind of method (method of storing machines and method of providing machines to patients) is employed to reuse the medicines. The presentation unit 113 can provide health care workers with information on the reuse of medical devices and medicines by presenting the learning results of the machine learning described above. The medical institution can effectively reduce the medical expenses by acquiring or sharing the learning result regarding the reuse with a specific medical institution or a plurality of medical institutions.

As described above, the learning unit 112 can automatically analyze a large number of data including the medical institution data D1, the patient data D2, the environment data D3, and other data. Therefore, it is possible to eliminate or reduce the trouble of analyzing a large number of these data by a human. Further, since the learning unit 112 performs analysis using various data, the assist system 100 can extract factors that affect the economic efficiency, management problems, and the like that have not been grasped by the manager of the medical institution.

Next, the presentation unit 113 will be described.

In the present embodiment, the presentation unit 113 periodically acquires the latest medical institution data D1, patient data D2, environment data D3, other data, and the like after the machine learning by the learning unit 112. Then, the presentation unit 113 applies the machine learning result of the learning unit 112 to the latest medical institution data D1, patient data D2, environment data D3, other data, and the like, so as to periodically present management policies to each medical institution to improve the economic efficiency of each medical institution. In accordance with an aspect, the operation policy that improves the economic efficiency of each medical institution is an operation policy that maximizes the profits of each medical institution. Thus, the presentation unit 113 periodically analyzes the latest medical institution data D1, patient data D2, and environment data D3 so as to present an optimal operation policy according to changes in patients in the region, changes in the environment surrounding each medical institution, and the like.

Specifically, for example, the presentation unit 113 can set an operation policy to increase a turnover ratio in a case where the number of patients is expected to increase and as a result of the analysis, it is determined that increasing the turnover ratio can improve the economic efficiency. In addition, for example, in a case where the number of patients is expected to decrease and it is determined that improving the quality of medical care can acquire patients and improve the economic efficiency, the presentation unit 113 presents an operation policy that improves the quality of medical care. In addition, the presentation unit 113 presents an operation policy that reduces the number of personnel and equipment inventory in a case where it is determined that the economic efficiency can be improved by reducing the number of personnel and equipment inventory due to the deterioration of the economic efficiency. Also, the presentation unit 113 presents an operation policy that changes the priority medical care in a case where the patients are deprived by another medical institution in the region, and it is determined that changing the priority medical care to a medical field lacking in the region can improve the economic efficiency.

In addition, for example, the presentation unit 113 presents an operation policy that increases the number of ambulances owned in a case where it is determined that increasing the number of ambulances allows the patients to be accepted before their condition deteriorates, and that medical expenses can be reduced, and thereby the economic efficiency can be improved.

In addition, for example, as illustrated in FIG. 7, in the region S to which the target medical institution 200a belongs, the presentation unit 113 acquires, from the learning unit 112, the surgery insufficient in the vicinity of the region where the target medical institution 200a is installed. As an example, in a case where there is a shortage of doctors or facilities capable of performing primary PCI in a given region, and it is determined that the economic efficiency of the target medical institution 200a can be improved when the target medical institution 200a is able to implement the primary PCI, the presentation unit 113 presents the operation policy to improve doctors, facilities, or the like so that the primary percutaneous coronary intervention (PCI) can be implemented. This not only can improve the economic efficiency of the target medical institution 200a, but can also contribute to regional medical care in the region S to which the target medical institution 200a belongs. In addition, it is possible to rescue the patients who are urgently transported due to a disease requiring an early response such as acute myocardial infarction.

At the time of emergency transport, for example, the presentation unit 113 may present the optimal medical institution to each medical institution, rescue squad, patient, or the like, as a destination based on information on whether or not each surgery of each of the medical institutions 200a and 200b in each region S can be performed, and information on the geographical range T that each of the medical institutions 200a and 200b can handle for each disease in a case where a patient is urgently transported. As a result, it is possible to prevent a patient from selecting a medical institution that cannot perform the optimal surgery as a first transport destination.

When a medical institution manager or the like operates each medical institution based on the presented operation policy, it can improve the operation of each of the medical institutions efficiently and improve the economic efficiency. In addition, since the economic efficiency of a plurality of medical institutions belonging to the region is improved, medical care in the entire region can be stabilized. Note that, the timing at which the presentation unit 113 presents the operation policy is not limited to the above. For example, the presentation unit 113 may present the operation policy in a case where there is a presentation request for an operation policy from a medical institution manager or the like.

Further, the presentation unit 113 applies the machine learning result of the learning unit 112 to the latest medical institution data D1, patient data D2, environment data D3, other data, and the like, and then, in a case where it is estimated that there is a problem with the patient's health, the presentation unit 113 can present the medical treatment policy to the patient. In addition, in a case where the patient's health condition has deteriorated, the patient can fill out a medical interview sheet and request for presentation of a medical treatment policy to the assist system 100. In this case, the presentation unit 113 applies the machine learning result of the learning unit 112 to the latest medical institution data D1, patient data D2 (including the medical interview sheet), environment data D3, other data, and the like, and then presents the medical treatment policy to the patient. Specifically, for example, the presentation unit 113 can present an expected disease name to the patient. Further, for example, the presentation unit 113 can present a recommended medical institution and a treatment schedule to the patient. As described above, the assist system 100 assists the operation of each medical institution by presenting the medical treatment policy to the patient.

The presentation unit 113 presents the basis for presenting the operation policy together with the operation policy. That is, the presentation unit 113 presents the basis for determining that the economic efficiency of each medical institution can be improved by the operation policy. The method of presenting the basis is not particularly limited, and can be represented by various methods such as a sentence, a numerical value, a graph, and a table. Therefore, the user can perform the operation in accordance with the operation policy with a sense of satisfaction.

Figure 5:
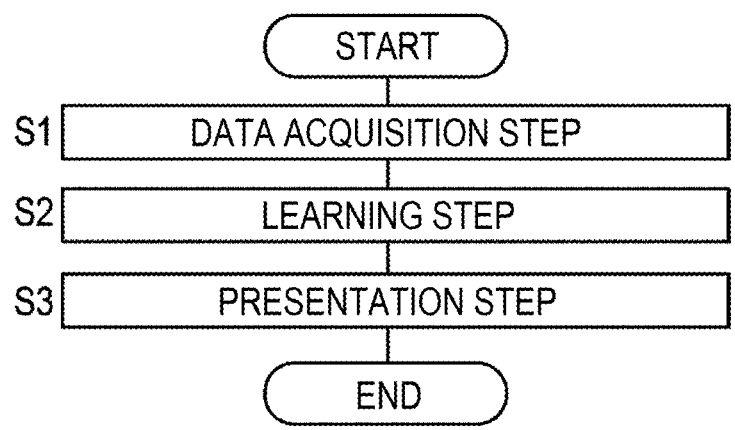
FIG. 5 is a flowchart illustrating an assist method according to an embodiment disclosed here.

FIG. 5 and FIGS. 6A and 6B are diagrams for explaining an assist method according to the present embodiment. Hereinafter, the assist method according to the present embodiment will be described with reference to FIG. 5 and FIGS. 6A, and 6B.

When summarizing with reference to FIG. 5, the assist method includes a data acquisition step S1 of acquiring medical institution data D1, patient data D2, environment data D3, and other data for machine learning, a learning step S2 of performing the machine learning using the medical institution data D1, the patient data D2, the environment data D3, and other data for machine learning, and a presentation step S3 of presenting an operation policy that improves economic efficiency of each medical institution and presenting a medical treatment policy to each patient, based on the result of the machine learning. Hereinafter, each step will be described.

First, the data acquisition step S1 will be described.

In the data acquisition step S1, the data acquisition unit 111 acquires the medical institution data D1, the patient data D2, the environment data D3, and other data for machine learning, and stores these data in the storage unit 120. The timing at which the data acquisition unit 111 acquires the medical institution data D1, the patient data D2, and the environment data D3 is not particularly limited, and for example, the data acquisition unit 111 may acquire the data at predetermined time intervals or at a timing when these data change. Further, the data acquisition unit 111 acquires the medical institution data D1, the patient data D2, and the environment data D3 over a predetermined period, and stores the acquired data in the storage unit 120. Therefore, a large amount of data sufficient for performing the machine learning is stored in the storage unit 120.

Next, the learning step S2 will be described.

In the learning step S2, the learning unit 112 performs machine learning using the medical institution data D1, patient data D2, environment data D3, and other data for machine learning stored in the storage unit 120. As a result, the learning unit 112 extracts rules, criteria, and the like related to the economic efficiency of the medical institution.

Next, the presentation step S3 will be described.

The presentation unit 113 acquires the medical institution data D1, patient data D2, environment data D3, other data, and the like, from the latest medical institutions, patients, and environmental information providers. Next, the presentation unit 113 applies the machine learning result of the learning unit 112 to the latest medical institution data D1, patient data D2, environment data D3, other data, and the like, so as to present the operation policy and the basis for presentation to each medical institution to improve the economic efficiency of each medical institution. Specifically, as illustrated in FIG. 6A, the presentation unit 113 can present the operation policy and the basis for presentation to each medical institution by displaying the operation policy and the basis for presentation on a display 210 of the medical institution terminal 200. Note that, in FIG. 6A, examples of the operation policies for improving the economic efficiency include "inpatients are switched to outpatient visits when they become chronic", "it is good to make the distance between the nurse station and the bed closer", and "it is advisable that a highly qualified doctor should be in charge of a highly difficult surgery". In addition, in FIG. 6A, as the basis for the presentation, it is expected that the number of patients will increase in the future, and switching to the above management policy will increase turnover ratio and improve the economic efficiency, and a graph showing the transition of the expected number of patients will be shown. The presentation unit 113 can be configured to periodically perform a flow from the acquisition of the latest data to the presentation.

Further, the presentation unit 113 can apply the machine learning result of the learning unit 112 to the latest medical institution data D1, patient data D2, environment data D3, other data, and the like, and then, in a case where it is estimated that there is a problem with the patient's health, the presentation unit 113 can present the medical treatment policy to the patient. In addition, in a case where the patient's health condition has deteriorated, the patient can fill out a medical interview sheet and request for presentation of a medical treatment policy to the assist system 100. In this case, the presentation unit 113 applies the machine learning result of the learning unit 112 to the latest medical institution data D1, patient data D2 (including the medical interview sheet), environment data D3, other data, and the like, and then presents the medical treatment policy to the patient. Specifically, for example, as illustrated in FIG. 6B, the presentation unit 113 can present, to the patient, an expected disease name, necessity of a medical treatment, and a medical treatment policy in a case where the necessity of the medical treatment is relatively high by displaying a recommended medical institution and a medical treatment schedule (including a clinical path) on a display 310 of a patient terminal 300. FIG. 6B illustrates an example in which the expected disease name is "ischemic heart disease", the necessity of medical treatment is relatively "high", and the recommended medical institution is "medical institution A". In a case where the necessity of the medical treatment is relatively low, the contact information of a local consultation service or the like may be displayed to prompt the patient to consult before receiving medical treatment.

Note that, in a case where the medical institution is operated or the patient receives a medical treatment based on the operation policy and the medical treatment policy, the data acquisition unit 111 may acquire data such as medical institution data D1, patient data D2, and environment data D3 again. Then, the learning unit 112 may perform machine learning again using the newly acquired data.

As described above, the assist system 100 according to the present embodiment includes the learning unit 112 that performs machine learning using medical institution data D1 including operation data D11 relating to the operation of the medical institution and economic data D12c relating to the economic efficiency, patient data D2 relating to the patient in the region to which the medical institution belongs, and environment data D3 relating to environment surrounding the medical institution, and the presentation unit 113 that presents the operation policy for improving the economic efficiency of the medical institution based on the result of the machine learning.

In accordance with an aspect, the assist system 100 can present the operation policy that improves the economic efficiency of the medical institution based on the results of the machine learning using the medical institution data D1, patient data D2, and environment data D3. Therefore, when a medical institution manager or the like operates the medical institution based on the presented operation policy, the operation policy can improve the operation of medical institutions efficiently and improve the economic efficiency.

In addition, the presentation unit 113 presents the basis for presenting the operation policy together with the operation policy. Therefore, the user can know the basis of the operation policy presented by the assist system, and can perform the operation in accordance with the operation policy with a sense of satisfaction.

In addition, the operation data D11 includes at least one of data on medical treatment subjects, doctors, equipment, layouts, and clinical paths of the medical institution. Therefore, the assist system 100 can present these improvement methods.

As described above, the assist method according to the present embodiment includes the learning step S2 of performing machine learning using medical institution data D1 including operation data D11 relating to the operation of the medical institution and economic data D12c relating to the economic efficiency, patient data D2 relating to the patient in the region to which the medical institution belongs, and environment data D3 relating to environment surrounding the medical institution, and the presentation step S3 of presenting the operation policy for improving the economic efficiency of the medical institution based on the result of the machine learning. Therefore, when a medical institution manager or the like operates the medical institution based on the presented operation policy, it can improve the operation of medical institutions efficiently and improve the economic efficiency.

As described above, the assist program according to the present embodiment can include performing machine learning using medical institution data D1 including operation data D11 relating to the operation of the medical institution and economic data D12c relating to the economic efficiency, patient data D2 relating to the patient in the region to which the medical institution belongs, and environment data D3 relating to environment surrounding the medical institution, and presenting the operation policy for improving the economic efficiency of the medical institution based on the result of the machine learning. Therefore, when a medical institution manager or the like operates the medical institution based on the presented operation policy, it can improve the operation of medical institutions efficiently and improve the economic efficiency.

As described above, the assist system, the assist method, and the assist program according to the present disclosure have been described through the embodiments; however, the present disclosure is not limited to each configuration described in the specification, but can be appropriately modified based on the description in the claims.

For example, the assist system, the assist method, and the assist program according to the above embodiment are intended to assist the operation of a plurality of medical institutions belonging to a certain region; however, the number of medical institutions to be assisted is not particularly limited as long as it is one or more.

In addition, the assist system, the assist method, and the assist program according to the above embodiment have a function of presenting the medical treatment policy to the patient, but may not have a function of presenting the medical treatment policy to the patient.

In addition, the data used for the machine learning by the assist system according to the present disclosure is not particularly limited as long as it uses at least medical institution data, patient data, and environment data. For example, the assist system need not use other data for the machine learning as in the assist system according to the above embodiment.

Further, in the assist system according to the above embodiment, the learning unit performs the machine learning using the algorithm of the supervised learning; however, the algorithm used by the learning unit for the machine learning may be the algorithm of the unsupervised learning or the algorithm of the reinforcement learning. In addition, the learning unit may perform the machine learning using a plurality of types of algorithms.

Further, in the system according to the above embodiment, there has been described that the data acquisition unit acquires the medical institution data, patient data, and environment data for the machine learning over a predetermined period. However, the data used for the machine learning, for example, past medical institution data, patient data, and environment data stored in a server or the like of each medical institution may be acquired.

In addition, means and method for performing various processes in the assist system according to the above embodiment can be realized by either a dedicated hardware circuit or a programmed computer. The assist program may be provided by a computer-readable recording medium such as a compact disc read only memory (CD-ROM) or may be provided online via a network such as the Internet. In this case, the program recorded on the computer-readable recording medium is generally transferred to and stored in a storage unit such as a hard disk. Further, the assist program may be provided as independent application software.

The detailed description above describes embodiments of an assist system, an assist method, and an assist program for assisting the operation of the medical institution. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. An assist system that assists an operation of a plurality of medical institutions, the system comprising:
a processor configured to:
perform machine learning using medical institution data including operation data relating to the operation of the plurality of medical institutions and economic data relating to an economic efficiency, patient data relating to patients in a region to which the plurality of medical institutions belong, medical device data relating to which medical devices or components of the medical devices are reusable, and environment data relating to an environment surrounding each of the plurality of medical institutions;
present an operation policy for improving the economic efficiency of each of the plurality of medical institutions belonging to the region based on a result of the machine learning;
present a medical treatment policy to each patient based on a result of the machine learning based on a relationship between the patient data, the medical device data, the environment data, and medical data, the medical data including disease name, symptoms, and necessity of medical treatment for each patient, and wherein the presented medical treatment policy includes a recommendation of a medical institution from the plurality of medical institutions and a treatment schedule for each patient that improves the economic efficiency of the each of the plurality of medical institutions belonging to the region based on the result of the machine learning;
acquire latest medical institution data, latest patient data, latest medical device data, and latest environment data for the each of the plurality of medical institutions after the performing of the machine learning;
apply the machine learning result to the latest medical institution data, the latest patient data, the latest medical device data, and the latest environment data for the each of the plurality of medical institutions; and present management policies to the each of the plurality of medical institutions based on the machine learning result applied to the latest medical institution data, the latest patient data, the latest medical device data, and the latest environment data.

2. The assist system according to claim 1, wherein the processor is configured to present a basis for presenting the operation policy together with the operation policy.

3. The assist system according to claim 1, wherein the operation data includes at least one of data on medical treatment subjects, doctors, equipment, layouts, and clinical paths of the plurality of medical institutions.

4. The assist system according to claim 1,
wherein the medical institution data is obtained from the plurality of the medical institutions over a predetermined period; and
wherein the environment data relating to the environment surrounding each of the medical institutions includes one or more of weather, temperature, humidity, sunshine duration, and diseases that are prevalent in the region.

5. The assist system according to claim 1, wherein the processor is configured to use a supervised learning regression or classification algorithm to perform the machine learning.

6. The assist system according to claim 1, wherein the processor is configured to present the operation policy on a display of a medical institution terminal.

7. The assist system according to claim 1, wherein the machine learning includes analyzing input data using an algorithm, extracting useful rules and criteria from the analysis of the input data, and developing the algorithm.

8. The assist system according to claim 7, wherein the algorithm of the machine learning is a supervised learning algorithm, an unsupervised learning algorithm, and/or a reinforcement learning algorithm.

9. An assist method of assisting an operation of a plurality of medical institutions, the method comprising:
performing machine learning using medical institution data including operation data relating to the operation of the plurality of medical institutions and economic data relating to an economic efficiency, patient data relating to patients in a region to which the plurality of medical institutions belong, medical device data relating to which medical devices or components of the medical devices are reusable, and environment data relating to an environment surrounding each of the plurality of medical institutions;
presenting an operation policy for improving the economic efficiency of each of the plurality of medical institutions belonging to the region based on a result of the machine learning;
presenting a medical treatment policy to each patient based on a result of the machine learning based on a relationship between the patient data, the environment data, and medical data, the medical data including disease name, symptoms, and necessity of medical treatment for each patient, and wherein the presented medical treatment policy includes a recommendation of a medical institution from the plurality of medical institutions and a treatment schedule for each patient that improves the economic efficiency of the each of the plurality of medical institutions belonging to the region based on the result of the machine learning;
acquiring latest medical institution data, latest patient data, latest medical device data, and latest environment data for the each of the plurality of medical institutions after the performing of the machine learning;
applying the machine learning result to the latest medical institution data, the latest patient data, the latest medical device data, and the latest environment data for the each of the plurality of medical institutions; and
presenting management policies to the each of the plurality of medical institutions based on the machine learning result applied to the latest medical institution data, the latest patient data, the latest medical device data, and the latest environment data.

10. The assist method according to claim 9, further comprising:
presenting a basis for presenting the operation policy together with the operation policy.

11. The assist method according to claim 9, wherein the operation data includes at least one of data on medical treatment subjects, doctors, equipment, layouts, and clinical paths of the plurality of medical institutions.

12. The assist method according to claim 9, further comprising:
obtaining the medical institution data from the plurality of the medical institutions over a predetermined period; and
wherein the environment data relating to the environments surrounding each of the region includes one or more of weather, temperature, humidity, sunshine duration, and diseases that are prevalent in the region.

13. The assist method according to claim 9, further comprising:
using a supervised learning regression or classification algorithm to perform the machine learning.

14. The assist method according to claim 9, further comprising:
presenting the operation policy on a display of a medical institution terminal.

15. The assist method according to claim 9, wherein the machine learning includes analyzing input data using an algorithm, extracting useful rules and criteria from the analysis of the input data, and developing the algorithm.

16. The assist method according to claim 15, wherein the algorithm of the machine learning is a supervised learning algorithm, an unsupervised learning algorithm, and/or a reinforcement learning algorithm.

17. A non-transitory computer readable medium (CRM) storing computer program code executed by a computer processor that executes a process of assisting an operation of a plurality of medical institutions, the process comprising:
performing machine learning using medical institution data including operation data relating to the operation of the plurality of medical institutions and economic data relating to an economic efficiency, patient data relating to patients in a region to which the plurality of medical institutions belong, medical device data relating to which medical devices or components of the medical devices are reusable, and environment data relating to an environment surrounding each of the plurality of medical institutions;
presenting an operation policy for improving the economic efficiency of each of the plurality of medical institutions belonging to the region based on a result of the machine learning;
present a medical treatment policy to each patient based on a result of the machine learning based on a relationship between the patient data, the environment data, and medical data, the medical data including disease name, symptoms, and necessity of medical treatment for each patient, and wherein the presented medical treatment policy includes a recommendation of a medical institution from the plurality of medical institutions and a treatment schedule for each patient that improves the economic efficiency of the each of the plurality of medical institutions belonging to the region based on the result of the machine learning;

acquiring latest medical institution data, latest patient data, latest medical device data, and latest environment data for the each of the plurality of medical institutions after the performing of the machine learning;

applying the machine learning result to the latest medical institution data, the latest patient data, the latest medical device data, and the latest environment data for the each of the plurality of medical institutions; and presenting management policies to the each of the plurality of medical institutions based on the machine learning result applied to the latest medical institution data, the latest patient data, the latest medical device data, and the latest environment data.

18. The computer readable medium according to claim 17, further comprising:
presenting a basis for presenting the operation policy together with the operation policy.

19. The assist system according to claim 1, wherein the result of the machine learning for the treatment schedule for each patient includes consideration of a patient's address and transportation means, priority medical care of each of the plurality of medical institutions, congestion status of each of the plurality of medical institutions, and economic efficiency of each of the plurality of medical institutions.

20. The assist system according to claim 1, wherein the processor is configured to generate the medical treatment policy for a patient in response to receipt of a request for the medical treatment policy from the patient.

* * * * *